United States Patent
Yaszemski et al.

(10) Patent No.: US 7,642,300 B2
(45) Date of Patent: Jan. 5, 2010

(54) HYDROXYAPATITE GRAFTED FUMARATE BASED MACROMERS FOR BIODEGRADABLE COMPOSITES

(76) Inventors: Michael J. Yaszemski, 2806 15th Ave. SW., Rochester, MN (US) 55902; Bradford L. Currier, 2005 Merrihills Dr. SW., Rochester, MN (US) 55902; Esmaiel Jabbari, 1510 Berkeley Rd., Columbia, SC (US) 29205; Lichun Lu, 734 27th St. NW., Rochester, MN (US) 55901

(*) Notice: Subject to any disclaimer, the term of this patent is extended or adjusted under 35 U.S.C. 154(b) by 294 days.

(21) Appl. No.: 10/562,591

(22) PCT Filed: Jun. 29, 2004

(86) PCT No.: PCT/US2004/020842

§ 371 (c)(1),
(2), (4) Date: Jun. 13, 2006

(87) PCT Pub. No.: WO2005/019313

PCT Pub. Date: Mar. 3, 2005

(65) Prior Publication Data

US 2006/0241246 A1    Oct. 26, 2006

Related U.S. Application Data

(60) Provisional application No. 60/484,215, filed on Jul. 1, 2003.

(51) Int. Cl.
*C08F 297/02* (2006.01)
*C08F 297/00* (2006.01)

(52) U.S. Cl. ............... 523/113; 523/114; 523/115; 523/116; 424/424

(58) Field of Classification Search ............... 523/113, 523/114, 115, 116; 424/423, 424
See application file for complete search history.

(56) References Cited

U.S. PATENT DOCUMENTS 4,668,295 A    5/1987    Bajpai
5,085,861 A *  2/1992    Gerhart et al. ........... 424/78.17

OTHER PUBLICATIONS

International Search Report and Written Opinion Under Date of Mailing of Dec. 16, 2004, in connection with International Patent Application No. PCT/US2004/020842.

* cited by examiner

*Primary Examiner*—Irina S Zemel

(57) ABSTRACT

A composition is disclosed which comprises (i) a macromer prepared by reacting an unsaturated diacid having a carbon-carbon double bond and a saturated diacid, and (ii) a bioactive ceramic grafted to the macromer. In one embodiment, the unsaturated diacid having a carbon-carbon double bond is fumaric acid, the saturated diacid is compatible with fumaric acid and poly(propylene fumarate) such as succinic acid, glutaric acid, adipic acid, pimelic acid, suberic acid, azelaic acid, sebacic acid and mixtures thereof, and the bioactive ceramic is hydroxyapatite. In another embodiment, hydroxyapatite is grafted with a biodegradable and crosslinkable macromer comprising silane units alternating with fumarate and adipate units.

22 Claims, 4 Drawing Sheets

US 7,642,300 B2

HYDROXYAPATITE GRAFTED FUMARATE BASED MACROMERS FOR BIODEGRADABLE COMPOSITES

CROSS-REFERENCES TO RELATED APPLICATIONS

This application claims priority from U.S. Provisional Patent Application No. 60/484,215 filed Jul. 1, 2003.

STATEMENT REGARDING FEDERALLY SPONSORED RESEARCH

This invention was made with government support under grant No. R01-AR45871-02 awarded by the National Institutes of Health. The government has certain rights in the invention.

BACKGROUND OF THE INVENTION

1. Field of the Invention

This invention relates to ceramic grafted macromers that are useful as a filler in biodegradable composites, and more particularly to the synthesis of hydroxyapatite grafted with fumarate based degradable and crosslinkable macromers for use as a filler in biodegradable composites.

2. Description of the Related Art

Bioactive ceramics such as hydroxyapatite have been used for a variety of applications including bone fixation devices and implant coating. Synthetic hydroxyapatite is especially attractive to serve as a filler material for biodegradable polymer-ceramic composites (see, for example, Lu et al., Synthetic bone substitutes, Curr. Opin., Orthop., 11 (2000) 383-390). Advantages include similarity in composition to bone mineral, bioactivity and promotion of cellular function, and osteoconductivity. Previous studies indicate that interfacial bonding between the hydroxyapatite surface and the matrix can significantly improve mechanical properties of polymer-ceramic composites (see, for example, Porter et al., Mechanical properties of a biodegradable bone regeneration scaffold, J. Biomech. Eng. 122 (2000) 286-288; Zhu et al., Mechanical properties of biodegradable poly(propylene fumarate)/bone fiber composites, Trans. Soc. Biomater., 25 (2002)260; and Deb et al., Hydroxyapatite-polyethylene composites; effect of grafting and surface treatment of hydroxyapatite, J. Mater. Sci.: Mater. Med., 7 (1996) 191-193).

Thus, there is a continuing need for improved methods for incorporating hydroxyapatite into biodegradable polymer-ceramic composites. In particular, there is a need for methods for achieving improved interfacial bonding between hydroxyapatite and the matrix of biodegradable polymer-hydroxyapatite composites.

SUMMARY OF THE INVENTION

The present invention provides for the synthesis of ceramic grafted degradable and crosslinkable macromers which can chemically bond to a biodegradable matrix. For instance, hydroxyapatite grafted with fumarate based degradable and crosslinkable macromers can be used as a filler in biodegradable composites. As a result, biodegradable and bioactive composites with improved mechanical properties can be developed for orthopedic applications.

In one aspect, the invention provides for the synthesis of a composition wherein a bioactive ceramic, hydroxyapatite, is grafted to a biodegradable and crosslinkable macromer comprising substituted or unsubstituted silane units alternating with fumarate and saturated diacid (e.g., adipate) units. The saturated diacid units serve as a flexible spacer between the rigid fumarate units.

In another aspect, the invention provides for a biodegradable composite including a polymeric matrix and the hydroxyapatite grafted macromer crosslinked to the matrix. The matrix has a carbon-carbon double bond, and in one embodiment is poly(propylene fumarate). The composite is suitable as a scaffold for tissue regeneration such as bone regeneration.

In yet another aspect, the invention provides a crosslinkable, biodegradable material including a polymer having a carbon-carbon double bond, the hydroxyapatite grafted macromer, and a crosslinking agent for crosslinking the polymer and the hydroxyapatite grafted macromer. The crosslinkable, biodegradable material may be used as a bone substitute or a bone cement. Preferably, the polymer is poly(propylene fumarate), and the crosslinking agent is a free radical initiator such as benzoyl peroxide.

These and other features, aspects, and advantages of the present invention will become better understood upon consideration of the following detailed description, drawings, and appended claims.

DETAILED DESCRIPTION OF THE INVENTION

Figure 1A:
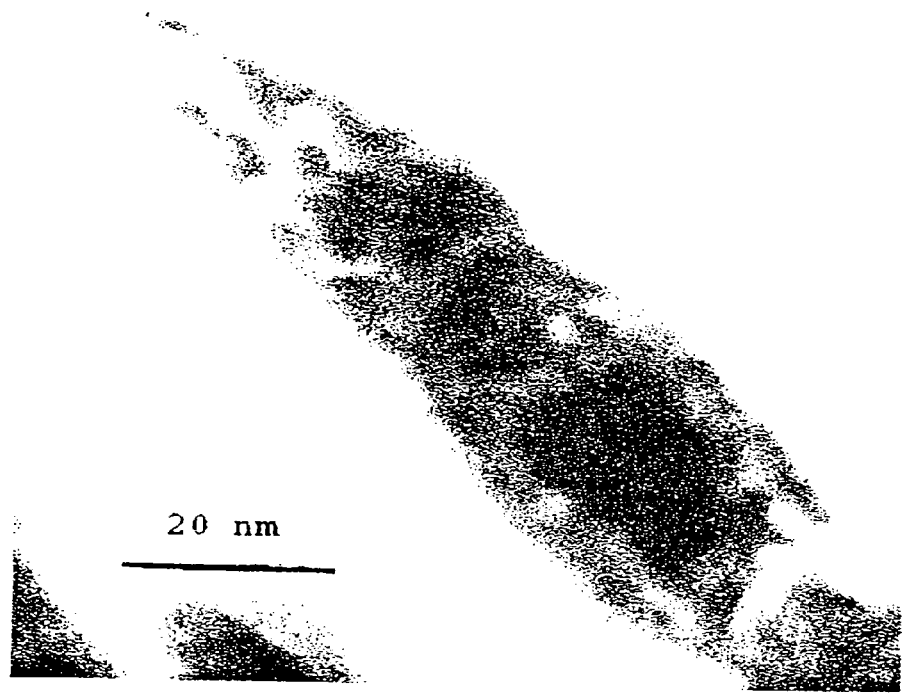
FIG. 1a is a TEM micrograph of one hydroxyapatite nanoparticle.

In this invention, a bioactive ceramic, such as hydroxyapatite ($Ca_{10}(PO_4)_6(OH)_2$) powder, is grafted with macromers that contain units derived from an unsaturated diacid having a carbon-carbon double bond (e.g., fumarate units). When used as a filler, the grafted macromer can be covalently crosslinked to a matrix containing unsaturated double bonds through the unsaturated double bonds found in the units derived from the unsaturated diacid (e.g., fumarate groups). In addition, the ester bonds in the unsaturated diacid (e.g., fumarate groups) are susceptible to hydrolytic cleavage, which promote the degradation of the macromer.

The macromer is prepared by reacting various components. The main component in the reaction mixture used to synthesize the macromer is the unsaturated diacid (e.g., fumaric acid) that contains an unsaturated double bond and two hydrolyzable ester groups. After the bioactive ceramic (e.g., hydroxyapatite) is grafted to the macromer and the grafted macromer is mixed with a biodegradable polymeric matrix having a carbon-carbon double bond, such as poly(propylene fumarate), the unsaturated carbon-carbon double bonds of the fumarate groups of the poly(propylene fumarate) in the matrix phase can inter-crosslink with the unsaturated carbon-carbon double bonds of the macromer in the grafted hydroxyapatite. This inter-crosslinking between the bioactive ceramic (e.g. hydroxyapatite) grafted macromer and the matrix phase significantly improves the mechanical strength of this biodegradable and bioactive composite especially in the torsional mode and in the bending mode.

The second component of the macromer is a spacer which imparts flexibility to the macromer therefore increasing the reactivity of the unsaturated diacid (e.g., fumarate groups) of the macromer with the fumarate groups of the matrix. The number of fumarate groups per macromer or the density of the fumarate groups on the graft can be controlled by varying the ratio of the spacer group to the fumarate group. The spacer is preferably a saturated diacid monomer compatible with fumaric acid and poly(propylene fumarate) selected from saturated diacid organic compounds including, without limitation, succinic acid, glutaric acid, adipic acid, pimelic acid, suberic acid, azelaic acid, sebacic acid, and the like. By 'compatible', we mean the saturated diacid does not interfere with the reaction between fumaric acid and poly(propylene fumarate) and the saturated diacid does not degrade fumaric acid or poly(propylene fumarate).

The third component of the macromer is a silane coupling agent that links the main component to the spacer to form a macromer. Example silane coupling agents include substituted or unsubstituted silanes such as dichlorodimethylsilane that form substituted or unsubstituted silane links between the fumarate and spacer monomers to form a macromer.

The fourth component of the macromer is a capping agent that restricts the grafting to one end of the macromer chain. In one embodiment, the fourth component is selected from alkyl esters (e.g., monomethyl ester) of the spacer monomer.

The bioactive ceramic may be bioactive ceramic powders with particle sizes ranging from nanometers to micrometers. These sizes are suitable for grafting in this invention. By bioactive, we mean a substance which affects the structure or function of the body or which becomes biologically active or more active after it has been placed in a predetermined physiological environment. Hydroxyapatite ($Ca_{10}(PO_4)_6(OH)_2$) powder is the preferred bioactive ceramic, and preferably has a particle size of less than 10,000 nanometers. The bioactive ceramic may be treated to facilitate grafting to the macromer. In one embodiment, hydroxyapatite is silicated to facilitate grafting to the macromer.

An exemplary procedure for preparation of the macromer and grafting with fumaric acid as the main component, adipic acid as the spacer and adipic acid monomethyl ester as the capping agent is as follows. First, hydroxyapatite whiskers are silicated with sodium metasilicate.

Second, the end-capped macromer is synthesized. To prepare the macromer, fumaric acid, adipic acid, and adipic acid monomethyl ester are added to dimethylchlorosilane. Next, polycondensation of bis(dimethylchlorosilyl)-fumarate, bis(dimethylchlorosilyl)-adipate, and dimethylchlorosilyladipate monomethyl ester is carried out to obtain the fumarate-adipate macromer capped with adipic acid monomethyl ester at one end and with reactive chlorosilane at the other end. After completion of the polycondensation reaction, the reactive chlorosilane end of the macromer chains is quenched with excess methanol to obtain a macromer capped with adipic acid monomethyl ester and methoxysilane.

Third, the macromer is grafted to the surface of the hydroxyapatite nanoparticles. The macromer is dissolved in an acetone-water mixture and the silicated hydroxyapatite is added to the mixture. After, removal of acetone and water, the macromer and silicated hydroxyapatite are condensed to produce the macromer with grafted hydroxyapatite.

EXAMPLES

The following Examples have been presented in order to further illustrate the invention and are not intended to limit the invention in any way.

A. Experimental

For maximum interfacial interaction and extent of grafting, hydroxyapatite nanoparticles with average size of 50 nm. were used in this study. Hydroxyapatite (HA) whiskers (Berkely Advanced Biomaterials, San Leandro, Calif.) with long and short axis of 100 and 20 nm, respectively, were used for grafting (See FIG. 1a). The HA was silicated according to the method described in Krorasani et al., Modified hydroxyapatite reinforced PEMA bone cement, in Bone Ceramics, Yamamura, Kokubo and Nakamura, Eds., Kobunshi Kankokai, Kyoto, Japan, 1992, pp. 225-232. Briefly, 1 gram of sodium metasilicate (SMS) (Aldrich, Milwaukee, Wis.) was dissolved in 50 ml. of distilled deionized water (DDW), 1 gram of HA was added, and the mixture was stirred for 3 hours. The pH was adjusted to 6.8 with hydrochloric acid and the mixture was allowed to stir overnight. The mixture was centrifuged and the solid silicated HA (SiHA) product was dried in vacuum at 150° for 2 hours.

To prepare end-capped dimethyldichlorosilane alternating fumaric acid/adipic acid (SFA) macromer, the procedure in Najafi et al., Preparation of biodegradable poly[(dimethyldichlorosilane)-alt-(fumaric acid/sebasic acid)]-co-PEG block copolymer, *Polymer,* 43 (2002) 6363-6368, was modified to cap the chain ends of the macromer with methoxysilane and adipic acid monomethyl ester (mAA), respectively. All reactants were obtained from Aldrich and they were used as received. In a typical procedure, 0.2 mol fumaric acid (FA), 0.2 mol adipic acid (AA), and 0.045 mol of mAA were added to a three-neck reaction flask containing 1.335 mol of dimethylchlorosilane (DMCS) in dry nitrogen atmosphere and under stirring. The silation reaction was carried out under reflux for 12 hours and the evolved HCl was captured in aqueous NaOH. Next, polycondensation of bis(dimethylchlorosilyl) fumarate, bis(dimethylchlorosilyl)adipate, and dimethylchlorosilyladipate monomethyl ester was carried out under vacuum of 10 mmHg at 120° C. for 4 hours to obtain the SFA macromer capped with mAA at one end and with reactive chlorosilane at the other end. The DMCS by-product produced during the polycondensation reaction was continuously removed under vacuum. After completion of polycondensation reaction, the reactive chlorosilane end of the SFA chains was quenched with excess methanol to obtain SFA macromer capped with mAA and methoxysilane (mSi). Excess methanol was removed by rotovaporation; the macromer was redissolved in methylene chloride and precipitated twice in cold ether. The macromer was dried under vacuum for at least 12 hours and stored at −20° C. before grafting. For comparison, 3-acryloylpropyl trimethoxysilane (AcHA) was also grafted to SiHA using the same procedure.

The following procedure was used to graft the macromer to the surface of SiHA. The SFA macromer was dissolved in 50 ml. of 70/30 acetone-water mixture in a reaction flask and the SiHA was added to the solution in nitrogen atmosphere and under vigorous mixing. After, removal of acetone and water at 100° C., the macromer and SiHA were condensed at 120° for 2 hours. The reaction by-product, methanol, was continuously removed during the reaction. The grafted HA was washed at least 3 times with THF, centrifuged, and dried under vacuum. The product was stored at −20° C. until use.

$^1$H-NMR was used to confirm the presence of the fumarate and adipate groups in the macromer. $^1$H-NMR spectrum was recorded with a Bruker Avance 500 MHz system (Bruker Analytik GmbH, Rheinstetten, Germany) at ambient temperature. Pulse angle, pulse duration, delay time, acquisition time, resolution, and number of scans was 90°, 6 µsec, 7 s. 3 s. 0.17 Hz, and 32, respectively. Macromer solution was prepared with deuterated chloroform (99.8 atom % Deutertaed, Aldrich) at a concentration of 50 mg/ml containing 1% v/v trimethylsilane (TMS) as the internal standard.

FTIR, thermogravimetric analyzer (TGA), and energy-dispersive x-ray spectroscopy (EDS) were used to characterize the grafted hydroxyapatite. An FTS-40 FTIR (Bio-Rad, Hercules, Calif.) was used to collect the spectrum in a dry nitrogen atmosphere with 200 averaged scans and resolution of 2 cm$^{-1}$. The grafted HA was suspended by sonication in perfluorodecalin (Aldrich) and injected in a 10 µm×3 mm cavity between two CaF$_2$ disks (Wilmad Glass, Buena, N.J.). Perfluorodecalin between two CaF$_2$ disks was used as the reference cell.

A TGA 2050 thermogravimetric analyzer (TA Instruments, New Castle, Del.) was used to measure the extent of grafting. Approximately 5 mg. of the grafted hydroxyapatite was heated at a rate of 20° C./min in an air atmosphere and the weight loss was recorded as a function of time. The TGA was calibrated for weight and temperature using 100 mg class M standard and the curie temperature of nickel, respectively.

For energy-dispersive x-ray spectroscopy, the grafted hydroxyapatite powder was embedded in a Spurr resin inside a plastic BEEM capsule (Electron Microscopy Sciences, Fort Washington, Pa.) and it was allowed to polymerize overnight in a convection oven. The blocks were sectioned with an Ultra S cryoultramicrotome (Leica, Deerfield, Ill.) to a thickness of 80 nm. The unstained sections were mounted on copper grids and the emitted x-ray energy of the elements were collected using a Noran Vantage X-ray Microanalysis System (Noran Instruments, Middleton, Wis.) with a Philips CM12 STEM PW6030 transmission electron microscope (Philips, Eindhoven, Netherlands).

B. Results and Discussion

Figure 1B:
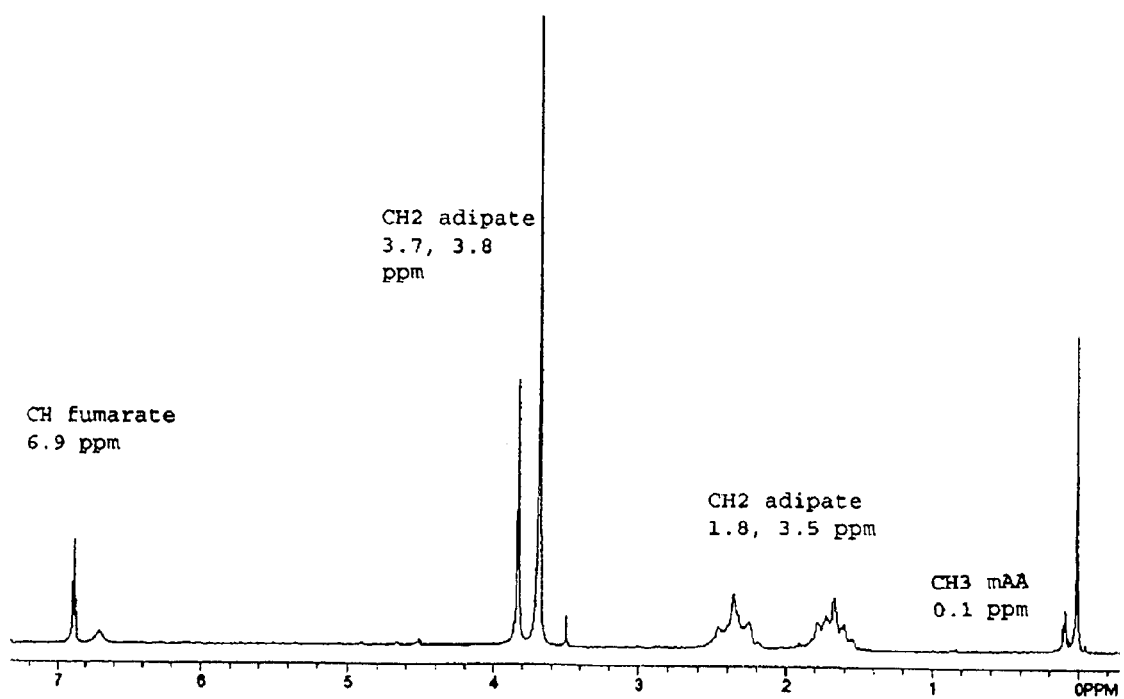
FIG. 1b is a H-NMR spectrum of a fumaric acid/adipic acid macromer.

The $^1$H-NMR spectrum of SFA macromer is shown in FIG. 1$b$. The shift with peak position at 6.9 ppm is due to hydrogens of fumarate groups of FA. The shifts with peaks centered at 3.7 and 3.8 ppm are due to methylene hydrogens of AA and mAA attached to two methylene groups. The shifts with peaks centered at 2.4 and 1.7 ppm are due to methylene groups hydrogens of AA and mAA attached to a methylene group and a carboxyl group. The shift with peak position at 0.1 ppm is due to methyl hydrogens of the methoxy group of mAA. According to the NMR spectrum, the ratio of FA:AA:mAA in the macromer is 1:2:1, which is different from the feed ration of 2:2:0.45. This indicates that AA and mAA are preferentially incorporated into the macromer compared to FA.

Figure 2:
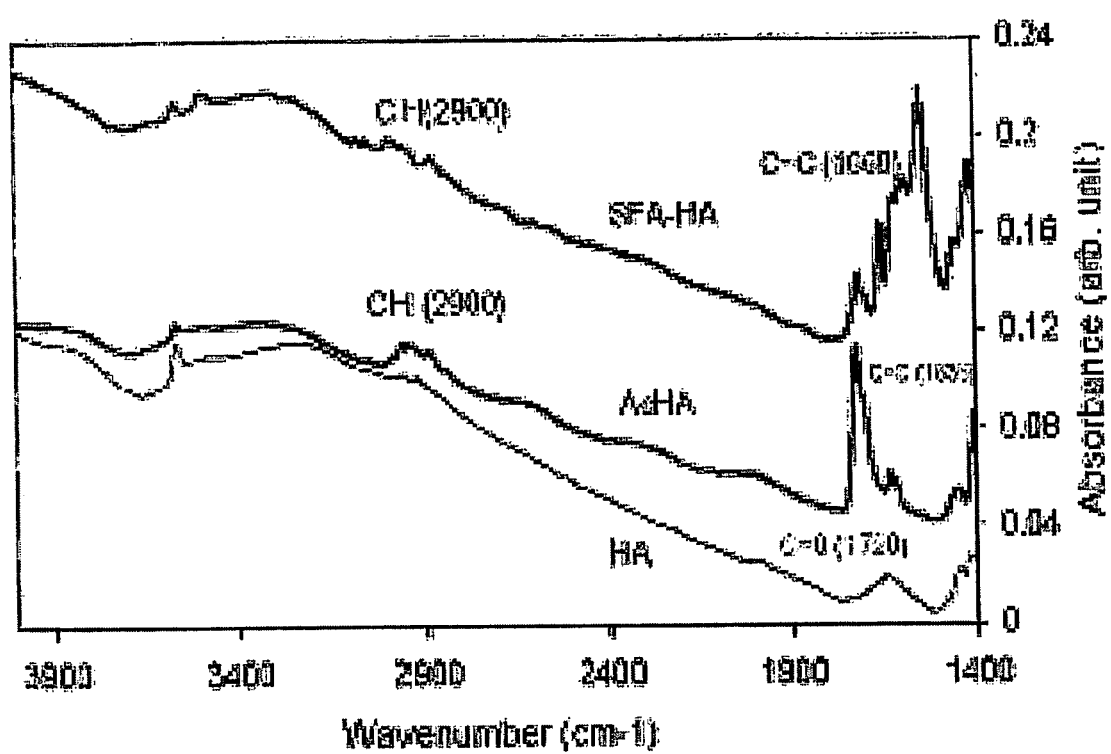
FIG. 2 is a FTIR spectrum of hydroxyapatite (HA), 3-acryloylpropyl trimethoxysilane grafted hydroxyapatite (AcHA), and fumaric acid/adipic acid grafted hydroxyapatite (SFA-HA).

FIG. 2 shows the FTIR of the HA versus AcHA and SFA grafted HA. The absorption bands with peak positions centered at 2900 and 2950 cm$^{-1}$ in the spectrum of AcHA are due to CH stretching vibrations of CH and CH$_2$ groups of 3-acryloxypropyl which is absent in the spectrum of HA. Likewise, the bands with peaks centered at 2885 and 2985 cm$^{-1}$ in the spectrum of SFA-HA are due to CH stretching vibrations of CH$_2$ groups of adipate which is absent in the HA spectrum. In the spectra of AcHA and SFA-HA, the band with peak centered at 1720 cm$^{-1}$ is due to C=O stretching vibration carboxyl groups which is absent in the HA spectrum. In the AcHA spectrum, the weak absorption band with peak centered at 1635 cm$^{-1}$ is due to C=C stretching vibration of CH$_2$=CHCOO-vinyl group of Ac which is absent in the spectra of HA and SFA-HA. In the SFA-HA spectrum, the weak absorption band with peak centered at 1660 cm$^{-1}$ is due to C=C stretching vibration of fumarate groups of SFA which is absent in the spectra of HA and AcHA.

Figure 3:
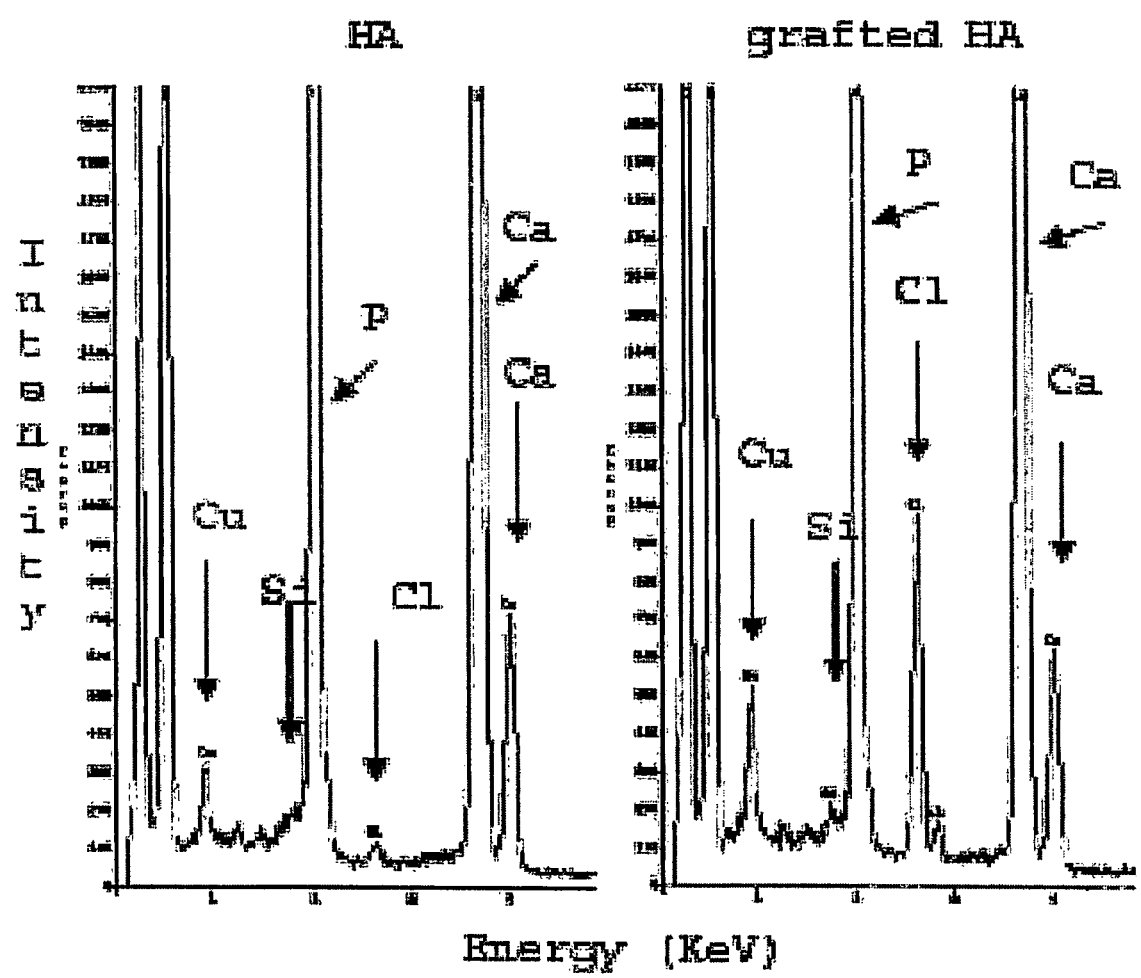
FIG. 3 is an energy-dispersive x-ray spectroscopy spectra of hydroxyapatite (left) and fumaric acid/adipic acid grafted hydroxyapatite (right).

In FIG. 3, the energy-dispersive x-ray spectroscopy spectrum of HA is compared with SFA-HA. Both spectra show emission bands at 2.0 KeV due to phosphorous in HA, at 3.7 and 4.0 KeV due to calcium in HA, and at 2.6 KeV due to chlorine in the embedding resin. In addition, there is a peak centered at 1.7 KeV due to Silicon in the SFA-HA spectrum due to silicate and dimethylsilane groups of the graft which is absent in the HA spectrum. The EDS and FTIR spectra indicate that the SFA macromer was successfully grafted to the HA surface. The presence of C=C absorption band in the FTIR spectrum of SFA-HA indicate that the grafted HA can participate in intra- and inter-molecular crosslinking.

Figure 4:
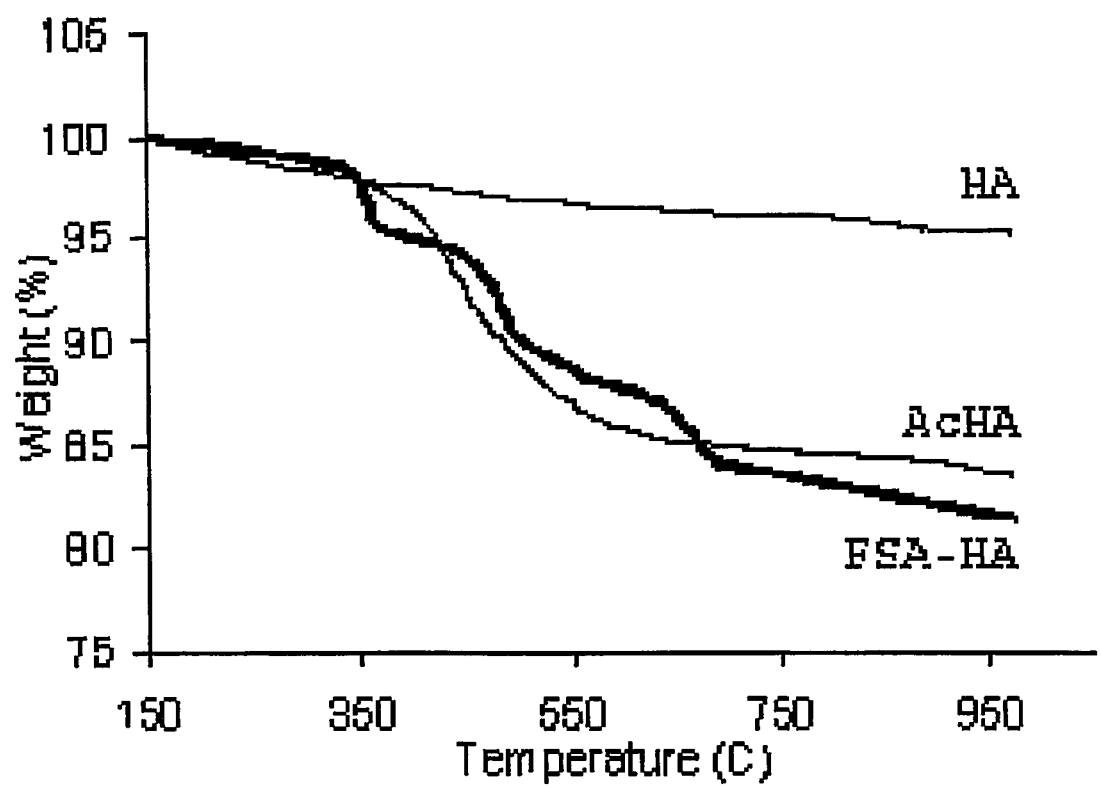
FIG. 4 is a graph of weight loss versus temperature for hydroxyapatite (HA), 3-acryloylpropyl trimethoxysilane grafted hydroxyapatite (AcHA), and fumaric acid/adipic acid grafted hydroxyapatite (SFA-HA).

The weight loss versus temperature for HA, AcHA, and SFA-HA is shown in FIG. 4. As the temperature was increased, the degradation of the graft in air for AcHA and SFA-HA commenced at 350° C. but it ended at 600° C. and 700° C., respectively. For AcHA graft, there was a continuous weight loss of the graft between temperatures of 350° and 600° C. However, for SFA-HA, the weight loss occurred step-wise in three steps centered at 350°, 500°, and 700° C., respectively. The step-wise degradation of SFA-HA graft was due to different degradation temperature of the constituents of the graft, which included fumarate, adipate, and dimethylsilane groups. According to thermogravimetric analyzer data in FIG. 4, the extent of grafting for AcA and SFA-HA were 12% and 15% by weight, respectively.

Thus, an example macromer including dimethylsilane units alternating with fumarate and adipate units was synthesized. The adipate and fumarate units of the macromer are degradable and the fumarate groups can be crosslinked. The macromer was capped at one end with methoxysilane group for grafting to silicated hydroxyapatite. The macromer was grafted to silicated hydroxyapatite and characterized by FTIR, energy-dispersive x-ray spectroscopy, and thermogravimetric analyzer. FTIR confirmed the presence of fumarate and adipate groups on the hydroxyapatite surface. Energy-dispersive x-ray spectroscopy confirmed the presence of silicon on the hydroxyapatite surface. According to thermogravimetric analyzer results, the extent of grafting was 15% by weight. These biodegradable and crosslinkable macromers grafted to hydroxyapatite can be useful for development of composite biomaterials in orthopedic tissue engineering applications.

INDUSTRIAL APPLICABILITY

The present invention relates to the synthesis of hydroxyapatite powder grafted with fumarate based degradable and crosslinkable macromers for use as a filler in biodegradable composites.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A composition comprising:
a macromer prepared by reacting an unsaturated diacid having a carbon-carbon double bond and a saturated diacid, wherein the unsaturated diacid having a carbon-carbon double bond is fumaric acid; and
a bioactive ceramic grafted to the macromer, wherein the bioactive ceramic is hydroxyapatite grafted to the macromer by way of silicate groups.

2. A biodegradable composite comprising:
(a) a polymeric matrix; and
(b) the composition of claim 1 crosslinked to the matrix.

3. The composite of claim 2 wherein:
the matrix has a carbon-carbon double bond.

4. The composite of claim 3 wherein:
the matrix comprises poly(propylene fumarate).

5. The composite of claim 2 wherein:
the composite is suitable as a scaffold for tissue regeneration.

6. The composite of claim 5 wherein:
the tissue is bone.

7. A crosslinkable, biodegradable material comprising:
a polymer having a carbon-carbon double bond;
the composition of claim 1, and
a crosslinking agent for crosslinking the polymer and the composition.

8. The material of claim 7 wherein:
the polymer comprises poly(propylene fumarate).

9. The material of claim 8 wherein:
the crosslinking agent is a free radical initiator.

10. The composition of claim 1 wherein:
the saturated diacid is selected from diacids compatible with fumaric acid and poly(propylene fumarate).

11. The composition of claim 10 wherein:
the saturated diacid is selected from succinic acid, glutaric acid, adipic acid, pimelic acid, suberic acid, azelaic acid, sebacic acid and mixtures thereof.

12. A composition comprising:
a macromer prepared by reacting an unsaturated diacid having a carbon-carbon double bond, a saturated diacid and a silane coupling agent; and
a bioactive ceramic grafted to the macromer.

13. The composition of claim 12 wherein:
the unsaturated diacid having a carbon-carbon double bond is fumaric acid, the saturated diacid is selected from diacids compatible with fumaric acid and poly(propylene fumarate), and the silane coupling agent is a dihalodialkylsilane.

14. The composition of claim 13 wherein:
the saturated diacid is selected from succinic acid, glutaric acid, adipic acid, pimelic acid, suberic acid, azelaic acid, sebacic acid and mixtures thereof.

15. The composition of claim 12 wherein:
the macromer is prepared by reacting the unsaturated diacid having a carbon-carbon double bond, the saturated diacid, the silane coupling agent, and an ester of the saturated diacid.

16. The composition of claim 15 wherein:
the saturated diacid is adipic acid,
the silane coupling agent is a dichlorodimethylsilane, and
the ester is a monomethyl ester of adipic acid.

17. The composition of claim 15 wherein:
the bioactive ceramic comprises hydroxyapatite particles having a particle size of less than 10,000 nanometers.

18. A composition comprising:
a macromer including silane units, units derived from an unsaturated diacid having a carbon-carbon double bond, and units derived from a saturated diacid; and
a bioactive ceramic grafted to the macromer.

19. The composition of claim 18 wherein:
the macromer includes silane units, fumarate units, and units derived from a saturated diacid, and
the bioactive ceramic is hydroxyapatite.

20. The composition of claim 18 wherein:
the macromer includes silane units, fumarate units, and adipate units, and the bioactive ceramic is hydroxyapatite.

21. The composition of claim 18 wherein:
the bioactive ceramic is hydroxyapatite.

22. The composition of claim 21 wherein:
the hydroxyapatite is grafted to the macromer by way of silicate groups.

* * * * *